United States Patent
Nishimura et al.

(10) Patent No.: US 6,613,940 B1
(45) Date of Patent: Sep. 2, 2003

(54) METHOD FOR CATALYTIC GAS PHASE OXIDATION

(75) Inventors: Takeshi Nishimura, Hyogo (JP); Masakatsu Mori, Hyogo (JP); Masatsugu Kitaura, Hyogo (JP); Osamu Dodo, Hyogo (JP); Daisuke Nakamura, Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 362 days.

(21) Appl. No.: 09/648,950

(22) Filed: Aug. 25, 2000

(30) Foreign Application Priority Data

Aug. 31, 1999 (JP) .......................... 11-246056

(51) Int. Cl.[7] .......................... C07C 51/16; C07C 45/00
(52) U.S. Cl. .................. 562/545; 562/532; 562/535; 562/542; 568/470
(58) Field of Search .................. 562/532, 535, 562/542, 545; 568/470; 165/107

(56) References Cited

U.S. PATENT DOCUMENTS

| 3,871,445 A | | 3/1975 | Wanka et al. |
| 4,203,906 A | * | 5/1980 | Takeda et al. .............. 549/248 |
| 4,657,741 A | | 4/1987 | Vogl .......................... 422/202 |
| 5,739,391 A | | 4/1998 | Ruppel et al. .............. 562/532 |
| 5,821,390 A | | 10/1998 | Ruppel et al. |

FOREIGN PATENT DOCUMENTS

| DE | 838598 | 9/1951 | |
| EP | 532325 A1 | 3/1993 | .............. B01J/8/06 |
| EP | 0987057 A1 | 3/2000 | .............. B01J/8/06 |
| GB | 2 007 523 A | 11/1978 | |

* cited by examiner

Primary Examiner—Alan L. Rotman
Assistant Examiner—Taylor V. Oh
(74) Attorney, Agent, or Firm—Mathews, Collins, Shepherd & McKay, P.A.

(57) ABSTRACT

In the reaction of catalytic gas phase oxidation by means of a shell-and-tube type reactor adapted to circulate a heating medium to the shell of the reactor through the medium of a circulation device connecting an annular conduit connected thereto, a method for the catalytic gas phase oxidation characterized by subjecting a part of the heating medium extracted from the shell of the reactor to heat exchange, introducing the heating medium resulting from the heat exchange into the proximity of a heating medium circulation inlet on the inlet side of the circulation device or the annular conduit on the outlet side of the reactor. The flow rate of the heating medium after the heat exchange is preferred to be in the range of 2–40 vol. % based on the flow rate of the heating medium within the shell of the reactor and the temperature difference of the heating medium at the inlet and the outlet to be in the range of 15–150° C. According to this invention, it is made possible to reduce evenly the hot spots in the reaction tubes, improve the yield of the product aimed at, and implement a reaction of catalytic gas phase oxidation of propylene or isobutylene.

8 Claims, 6 Drawing Sheets

→⊗ : temperature of reaction heat
→⊗ : places where measured heating medium temperature
× : places where measured hot spots

METHOD FOR CATALYTIC GAS PHASE OXIDATION

BACKGROUND OF THE INVENTION

1. Field of the Invention

This invention relates to a method for catalytic gas phase oxidation adapted to introduce a heating medium into a reactor for catalytic gas phase oxidation by means of a circulation device and characterized by that the introduction of the heating medium being cooled and then circulated into the reactor is effected in the proximity of the inlet to a heating medium circulation system equipped with the reactor or the outlet side of an annular conduit surrounding the reactor and the amount of the heating medium to be circulated is a prescribed quantity.

2. Description of Related Art

The reaction of catalytic gas phase oxidation using a shell-and-tube type reactor is a means generally used for efficiently removing the heat which is generated by the reaction. The shell-and-tube type reactor used herein has a plurality of reaction tubes built in the shell of the reactor. The reaction tubes packed in advance with a catalyst are supplied with the raw material gas for the reaction and caused to attain the reaction of catalytic gas phase oxidation and the shell of the reactor is meanwhile caused to circulate therein a heating medium capable of absorbing the heat of reaction and absorb the produced heat of reaction.

The reaction of catalytic gas phase oxidation using the shell-and-tube type reactor constructed as described above, however, tends to form a hot spot on the raw material inlet side of the tubes and, consequently entails the problem that the catalyst packed into the tubes is damaged and the selectivity of a target product is lowered by an ensuing excessive exothermic reaction. In the case of producing acrolein from propene by the reaction of catalytic gas phase oxidation, for example, how efficiently the heat of reaction is removed with a view to improving the yield of the target product constitutes itself a problem.

The official gazette of, U.S. Pat. No. 3,871,445, for example, discloses a shell-and-tube type reaction apparatus provided with a device for circulating a heat exchange medium and characterized by having a baffle plate disposed in the shell of a reactor and further having at least one annular conduit disposed at one intermediate portion at least for the purpose of leading in or leading out part of the heat exchange medium. Owing to this disposition of the baffle plate, the lateral flow velocity of the heat exchange medium is retained at a fixed level and the transfer of heat is fixed as well in the space intervening between the baffle plates. This apparatus uses the heat exchange medium by circulating it inside and outside the reactor. The heat exchange medium discharged from the reactor is cooled by a cooling device built in a circulation device and then introduced into the reactor.

The official gazette of U.S. Pat. No. 4,657,741 discloses a shell-and-tube type reaction apparatus having a device for circulation of a heating medium connected thereto and it has a plurality of circulation devices connected thereto. It is aimed at reducing the cost of construction concerning equipment, and space while accomplishing manufacture of a reaction product of uniform and fine quality in a high yield and, as asserted in the specification, is expected to warrant thoroughly uniform inflow and outflow of the heating medium by the use of a plurality of pumps and allow a prominent decrease in the requirement of output by shortening the maximum feed distance.

In addition thereto, the official gazette of U.S. Pat. No. 5,821,390 discloses a method for the catalytic gas phase oxidation of propene to acrolein and the simultaneous retention of specific selectivity and conversion rate by the use of a shell-and-tube type reactor, which method, by guiding a heating medium in a cocurrent flow and, at the same time, having a baffle plate disposed in the reactor, attains adjustment of the flow rate of the heating medium so that the temperature of the heating medium within the reactor increases in the range of 2–10° C. According to the method disclosed in the official gazette, the acrolein is obtained by subjecting the propene to catalytic gas phase oxidation using a complex metal oxide catalytically active at a temperature elevated in the shell-and-tube type reactor and meanwhile reducing the temperature of the hot spot.

When the heating medium introduced into the shell side of the reactor for the purpose of removing the heat of reaction brings no sufficient removal of the heat of reaction, the possibility that the temperature will rise excessively in the catalyst layer to increase a side reaction, lower the yield, promote the damage of the catalyst, and induce a runaway reaction is not denied. In this case, giving a decreased diameter and an increased heat transfer area to the reaction tubes as a measure for efficient removal of the heat of reaction results in increasing the number of reaction tubes thereby heightening the cost of the reactors.

The heat balance is computed by the balance between the amount of heat generated by the reaction and the amount of heat consumed by cooling. Even the apparatus which is disclosed in the official gazette of U.S. Pat. No. 3,871,445 ought to allow more efficient removal of heat, depending on the conditions of use thereof.

The invention disclosed in the official gazette of U.S. Pat. No. 4,657,741 contemplates providing a plurality of circulation pumps for ensuring uniform circulation of a heating medium. Solely with the pressure exerted by the circulating pump, the inherently uniform mixture will not be easily attained. The removal of heat with an excellent heat exchange ratio, therefore, will not be easily attained unless the heating medium to be circulated has a uniform temperature distribution before it is introduced into the reactor by the pump.

As is clear from the working example cited in the official gazette of U.S. Pat. No. 5,821,390, under the conditions which fix the amount of the heat to be generated, the power of the pump which is required for limiting the rise of the temperature of the heating medium to 1° C. is perfectly identical no matter whether the heating medium is fed in counter flow or in cocurrent flow inside the shell of the reactor.

The temperature of the hot spot generated in the reaction tubes have possibility to induce such things as deterioration of the catalyst. Particularly, the portion that reaches the highest temperature in all the reaction tubes tends to determine the rate of the removal of heat. As a result, the question how uniformly the heat of the reaction tubes is removed and the maximum value of the hot spot is reduced emerges as a problem. None of the techniques of prior art, however, has been capable of accomplishing the thorough removal of the heat.

Since the amount of heat to be removed is determined by the relation thereof with the amount of heat to be generated, the desirability of developing the most efficient method for removing the heat of the reaction without damaging the yield of the production for a fixed apparatus under fixed reaction conditions has been finding growing recognition.

SUMMARY OF THE INVENTION

The present inventor, in consequence of a study pursued concerning methods for the circulation of a heating medium in a shell-and-tube type reactor, has discovered that when the heating medium extracted from the shell of the reactor is circulated to a specific place in a circulation device, the heating medium which has undergone heat exchange and the heating medium which has been discharged from the shell of the reactor are mixed exceptionally efficiently. This invention has been perfected as a result. That is, the object mentioned above is accomplished as follows.

In the reaction of catalytic gas phase oxidation by means of a shell-and-tube type reactor adapted to circulate a heating medium to the shell of the reactor through the medium of a circulation device connecting an annular conduit connected thereto, this invention concerns a method for the catalytic gas phase oxidation characterized by subjecting a part of the heating medium extracted from the shell of the reactor to heat exchange, introducing the heating medium resulting from the heat exchange into the proximity of a heating medium circulation inlet on the inlet side of the circulation device or the annular conduit on the outlet side of the reactor, setting the flow rate of the heating medium after the heat exchange in the range of 2–40 vol. % based on the flow rate of the heating medium within the shell of the reactor, and setting the temperature difference between the heating medium after the heat exchange and the heating medium being introduced into the shell of the reactor in the range of 15–150° C.

This invention is capable of reducing the hot spot temperature because it enables the heating medium $10a$ (shown FIG. 1) being circulated within the reactor to be mixed very easily with the heating medium $10b$ (shown FIG. 1) which has been cooled and consequently allows the heating medium having uniform heat distribution to be introduced into the shell of the reactor by causing the heating medium which has been cooled and is ready for circulation to the shell-and-tube type reactor to be supplied to the position confronting the inlet to the heating medium circulation system in the circulation device or to the annular conduit through which the heating medium is extracted from the shell-and-tube reactor.

The above and other objects, features, and advantages of the present invention will become clear from the following description of the preferred embodiments.

DESCRIPTION OF THE PREFERRED EMBODIMENTS

In the reaction of catalytic gas phase oxidation by means of a shell-and-tube type reactor adapted to circulate a heating medium to the shell of the reactor through the medium of a circulation device connecting an annular conduit connected thereto, this invention concerns a method for the catalytic gas phase oxidation characterized by subjecting a part of the heating medium extracted from the shell of the reactor to heat exchange and introducing the heating medium resulting from the heat exchange into the proximity of a heating medium circulation inlet on the inlet side of the circulation device or the annular conduit on the outlet side of the reactor. A method which comprises extracting a part of a heating medium from the shell of a reactor, cooling the heating medium, and the then returning the cooled heating medium to the shell of the reactor already exists. The method of this invention is characterized by introducing the cooled heating medium to the proximity of an inlet to a heating medium circulating system on the inlet side of the circulation device or to the annular conduit on the outlet side of the reactor. It has been consequently ascertained that since the heating medium resulting from the cooling and the heating medium extracted from the shell of the reactor are uniformly mixed intimately and then introduced into the shell of the reactor, the decrease of the hot spot temperature is attained very uniformly.

Now, the mode of a preferred embodiment of the method of this invention for catalytic gas phase oxidation will be described below with reference to FIG. 1.

First, in a shell 1 of a shell-and-tube type reactor, a heating medium 10 is introduced via an annular conduit 11a disposed on the outer periphery of the shell 1 of the reactor, circulated in the interior of the shell 1 of the reactor, and discharged from the shell 1 of the reactor via an annular conduit 11b.

In this invention, in the heating medium 10, the heating medium which is discharged from within the reactor via a heating medium outlet 12 formed in the annular conduit, cooled by a heat exchanger not shown in the diagram, and finally circulated to the shell of the reactor is denoted as 10b and the heating medium which is passed through the annular conduit then circulated to the circulation device without being cooled by an external heat exchanger as 10a. In the relevant diagrams, the flows of the heating medium are denoted as 10, 10a, and 10b. This invention is characterized by introducing the heating medium 10b into the shell 1 of the reactor via the proximity of a heating medium circulating inlet 31 of a circulation device 30. The term "heating medium circulating inlet 31" as used herein designates an inlet part for the supply of the heating medium 10a from the annular conduit to the circulation device 30. A method which comprises extracting a part of a heating medium to the exterior and circulating the extracted heating medium into the shell 1 of the reactor has existed to date. It has injected the heating medium 10b which has been cooled to the proximity of a heating medium outlet 34 of the circulation device 30. The reason for choosing the proximity of the heating medium outlet 34 as the site for the introduction of the cooled heating medium 10b is that the prevention of useless absorption of heat by the cooled heating medium 10b is attained most efficiently by the introduction effected in this manner. As a result, the heating medium 10a and the heating medium 10b are not thoroughly mixed, introduced while retaining uneven heat distribution from the heating medium outlet 34 into the shell 1 of the reactor, prevented from uniformizing the heat distribution of the heating medium 10, and compelled to generate a hot spot of elevated temperature, induce damage of the catalyst and the deterioration of the selectivity, and cause the decrease in the rate of production aimed at.

According to this invention, the heating medium 10a and the heating medium 10b are mixed very efficiently by disposing a heating medium inlet 32 in the proximity of the heating medium circulating inlet 31 inside the circulation device 30 and introducing there through the heating medium 10b which has been cooled. Moreover, since the amount of the heat absorbed by the heating medium which is being moved in the circulation device is very small, the heating medium is capable of fully satisfactorily remove the heat of the reaction, uniformly preventing the abnormal elevation of the temperature of the hot spot, and reducing the amount of the heating medium being circulated.

The term "the proximity of the heating medium circulating inlet 31" which is a preferred position of the heating medium inlet 32 to introduce the heat to have been cooled into the shell 1 refers to the position at which the heating medium 10a introduced through the heating medium circulating inlet 31 is efficiently mixed within the circulation device 30 with the heating medium 10b which has undergone the heat exchange to prepare a heating medium having uniform heat distribution. The position which confronts the heating medium circulating inlet 31 as illustrated in FIG. 1 may be cited.

Figure 5:
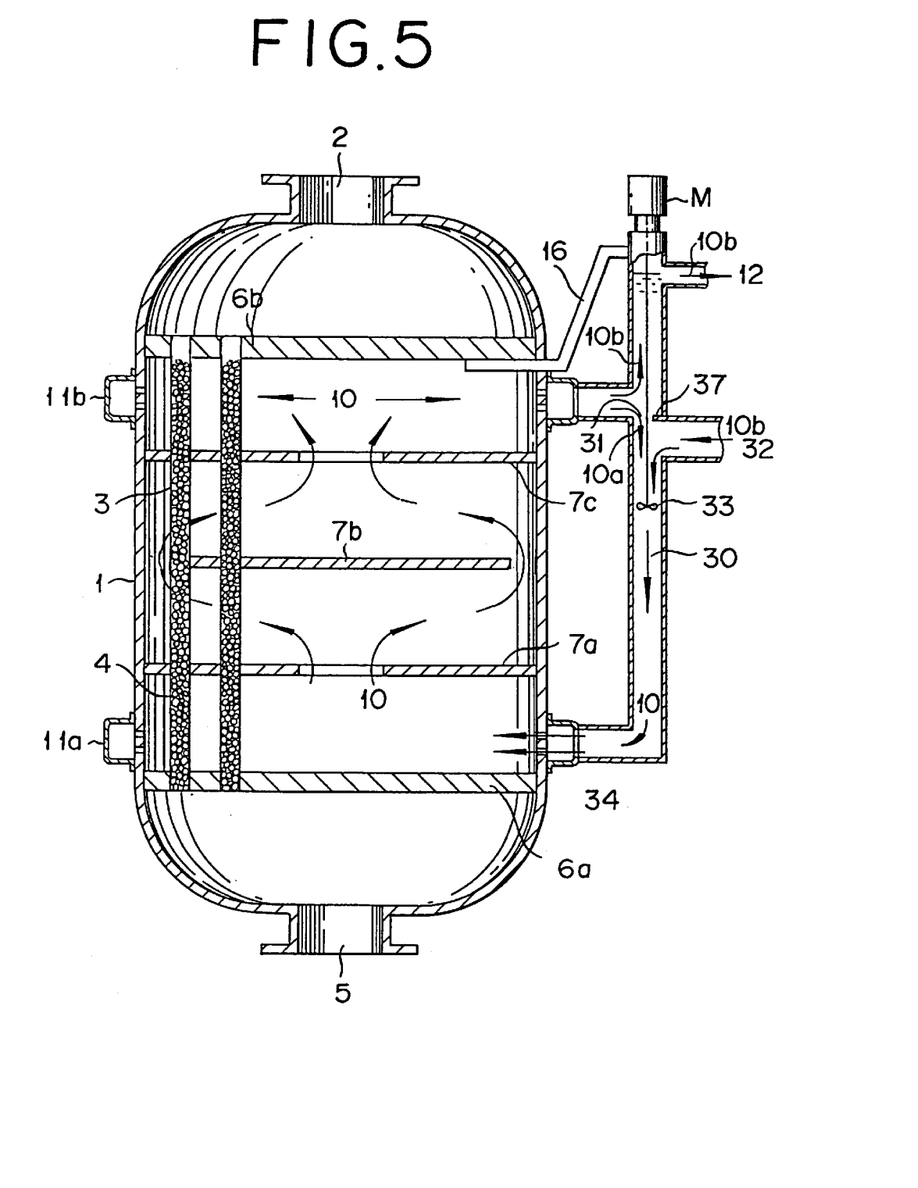
FIG. 5 is a cross section roughly illustrating a reactor of still another embodiment to be used for the reaction of catalytic gas phase oxidation according to this invention.

When the circulation device 30 is provided in the upper part thereof with a heating medium outlet 12 as illustrated in the mode of FIG. 5 which will be specifically described herein below, the introduction of the heating medium 10b through the position confronting the heating medium circulating inlet 31 proves disadvantageous in terms of the efficiency of heat because a part of the cooled heating medium 10b departs from the reactor through the heating medium outlet 12. In this case, the position which is nearest to the heating medium circulating inlet 31 in the circulation device 30 and, at the same time, farthest from the heating medium outlet 34, i.e. the outlet for the heating medium to be used for discharging the heating medium from the circulation device to the shell of the reactor is preferred in this invention. When the circulation device is provided therein with a plurality of heating medium circulation inlets 31, the heating medium 10b may be introduced to the proximity of any of such inlets 31. At any of these inlets 31, the heating medium 10b and the heating medium 10a are efficiently mixed.

Further, this invention permits the heating medium inlet 32 to be disposed in part of the annular conduit on the outlet side of the reactor which is connected to the heating medium circulation inlet of the circulation device. In this arrangement, the heating medium 10a and the heating medium 10b are already mixed when they are introduced into the circulation device 30 and the heating medium 10 of uniform heat distribution is easily prepared within the circulation device 30. In this case, the heating medium inlet 32 is preferred to be so positioned that it confronts the circulation device 30 and allows the mixture produced in the annular conduit to acquire a fully satisfactory retention time.

According to the method of this invention, an agitator may be provided or disposed in the place of a pump 33 adapted to effect efficient mixture of the heating medium 10a and the heating medium 10b in the circulation device 30. The agitator allows the heating medium of uniform heat distribution to be formed more efficiently. The heating medium 10 which has acquired uniform heat distribution as described above is introduced again from the annular conduit 11a into the shell 1 of the reactor via the heating medium outlet 34 of the circulation device 30.

Further, in this invention, the amount of the heating medium after the heat exchange mentioned above is in the range of 2–40 vol. % of the amount of the heating medium circulated inside the shell of the reactor and the temperature difference between the heating medium after the heat exchange at the heating medium inlet 32 of the circulation device 30 and the heating medium being introduced into the shell of the reactor is in the range of 15–150° C. The amount of the heating medium to be used for circulation is preferably in the range of 5–35 vol. %, particularly preferably 10–30 vol. %, of the total amount of the heating medium and the temperature difference is preferably in the range of 15–130° C., particularly preferably 20–120° C. To accomplish the removal of heat sufficient, it is convenient to increase the amount of the heating medium to be circulated. If the amount exceeds 40 vol. %, the excess will bring an economic disadvantage in excessively requiring the energy for the circulation.

Conversely, if it is less than 2 vol. %, the shortage will render sufficient cooling difficult. The fact that the temperature difference between the heating medium at the heating medium inlet 32 of the circulation device 30 and the heating medium being introduced into the shell of the reactor is small means that the amount of the cooled heating medium 10b advancing toward the reactor is large when the amount of the heat to be generated is fixed. If the temperature difference mentioned above is less than 15° C., the shortage will be at a disadvantage in requesting excessive energy for the circulation. The reduction of the hot spot temperature has the rate thereof determined by the removal of the heat at the highest hot spot temperature. In this invention, the removal of the heat generated in the tubes can be carried out fully satisfactorily by introducing heating medium having the temperature difference into the shell of the reactor even in the range of 15–150° C.

The term "temperature of the heating medium after the heat exchange" is to be interpreted as meaning the temperature of the heating medium to be introduced into the shell 1 of the reactor at the heating medium inlet 32 of the circulation device 30 or the annual conduit through which the heating medium is extracted from the shell-and-tube reactor, and the term "temperature of the heating medium being introduced into the shell of the reactor" as meaning the temperature of the heating medium 10 to be discharged from the circulation device 30 at the heating medium outlet 34.

In this invention, the heating medium 10b extracted from the shell of the reactor is preferred to undergo gas-liquid separation either before or after the heat exchange mentioned above or both. When the heating medium 10b to be used entrains air bubbles, it tends to form a gas pool in the upper tube sheet part inside the shell of the reactor. When the heating medium 10a and the heating medium 10b to be used as the heating medium have been gas-liquid separated, they are allowed to acquire uniform heat distribution easily. The methods which are available for the gas-liquid separation are represented by a method which avoids engulfing the gas by reducing the speed or securing the height of the liquid. Any of the other methods may be used instead.

The method of this invention can use a known shell-and-tube type reactor for implementing the reaction of this invention for catalytic gas phase oxidation. The shell-and-tube type reactor is preferred to be possessed of a pair of annular conduits 11a, 11b. The reason for this preference is that since the heating medium is supplied or discharged uniformly throughout the entire peripheral direction of the reactor through the medium of the annular conduit having an opening intermittently continuing throughout the entire periphery, the heating medium can be supplied uniformly and the hot spot temperature can be efficiently decreased.

Figure 2:
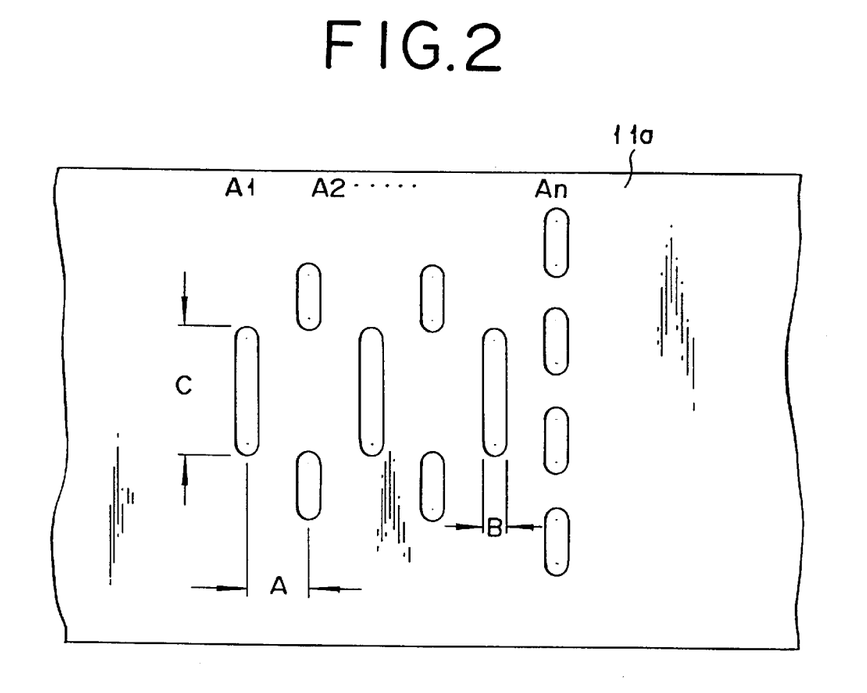
FIG. 2 is a side elevation illustrating an opening disposed in a annular conduit.

In this case, the annular conduit is preferred to be provided with a plurality of lines of openings which are permeable to the heating medium. This configuration will be described with reference to FIG. 2. The annular conduit 11a, for example, is provided with a plurality of lines of openings A1, A2. The center distance A between the nearest openings in the annular conduit, which may be identical or not identical in each of the rows, is in the range of 50–500 mm, preferably 100–400 mm, and more preferably 200–300 mm. If the center distance A mentioned above is less than 50 mm, the manufacture of the opening will be rendered difficult. Conversely, if it exceeds 500 mm, the uniform supply of the heating medium to the exterior of the reaction tubes will be rendered difficult. The number of openings in each of the lines of openings must be at least one or more. In FIG. 2, the line A1 is depicted as using one opening, the line A2 as using two openings, and the line An as using four openings. Since the numbers of openings existing in the individual lines may be different as described above, the distances between the nearest openings in the shell do not need to coincide with the center distance A mentioned above as illustrated in FIG. 2. The opening width B is set in the range of 5–50%, preferably 10–40%, and particularly preferably 20–30%, of the average center distance A mentioned above. If the opening width is less than 5%, the annular conduit will unduly gain in height. Conversely, if it exceeds 50%, the openings will be reduced in height and the supply of the heating medium throughout the wide region of the conduit will be rendered difficult. Further, the ratio of opening length C/opening width B is preferred to be in the range of 0.2–20. Incidentally, the center distance A does not need to be identical in all the annular conduits as mentioned above. By the same token, the opening width B does not need to be identical in all the annular conduits. The provision of such a plurality of openings allows the heating medium 10 to be uniformly brought in and out. These openings do not need to be particularly discriminated on account of shape. As concrete examples of the shape, circle, ellipsis, and rectangle may be cited.

Figure 1:
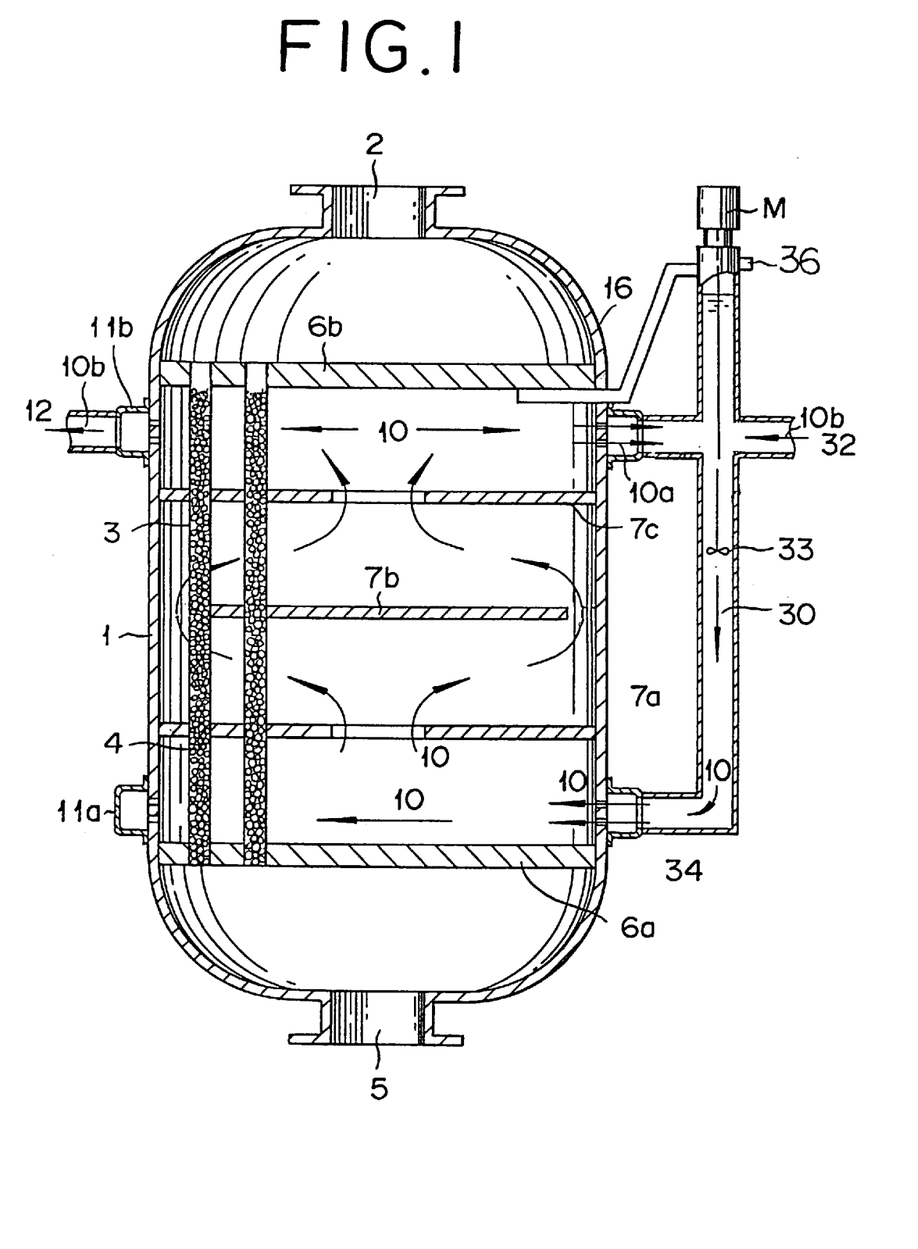
FIG. 1 is a cross section roughly illustrating a reactor to be used for the reaction of catalytic gas phase oxidation according to this invention.

The mode illustrated in FIG. 1 effects the supply of the raw material gas in a down flow from the upper part to the lower part of the reactor and introduces the heating medium 10 in the state of counter-flow relative to the raw material gas being supplied. In this invention, however, the raw material gas to be introduced into the reaction tube 3 in effecting the reaction of catalytic gas phase oxidation with the shell-and-tube type reactor 1 does not need to discriminate particularly between up-flow and down-flow. Further, the heating medium 10 does not need to discriminate particularly between cocurrent flow and counter flow. In any event, the removal of heat from the reaction tubes is attained uniformly so long as the heating medium 10a and the heating medium 10b are uniformly mixed intimately within the circulation device 30.

The method of this invention nevertheless prefers the heating medium 10 to be introduced in the up-flow. Generally, the heating medium 10 to be introduced tends to entrain the gas into the shell 1 of the reactor and give rise to an empty space devoid of the heating medium in the upper part of the shell 1 of the reactor. The up-flow introduction of the heating medium under added pressure facilitates the removal of the gas. Particularly, since such a pool of gas in the upper part of the shell allows no fully satisfactory local removal of heat on account of the absence of the heating medium and tends to give rise to abnormal rise of temperature, the up-flow introduction of the heating medium stabilizes the reaction stabilizes the reaction conditions by preventing the abnormal local rise of temperature.

Figure 3:
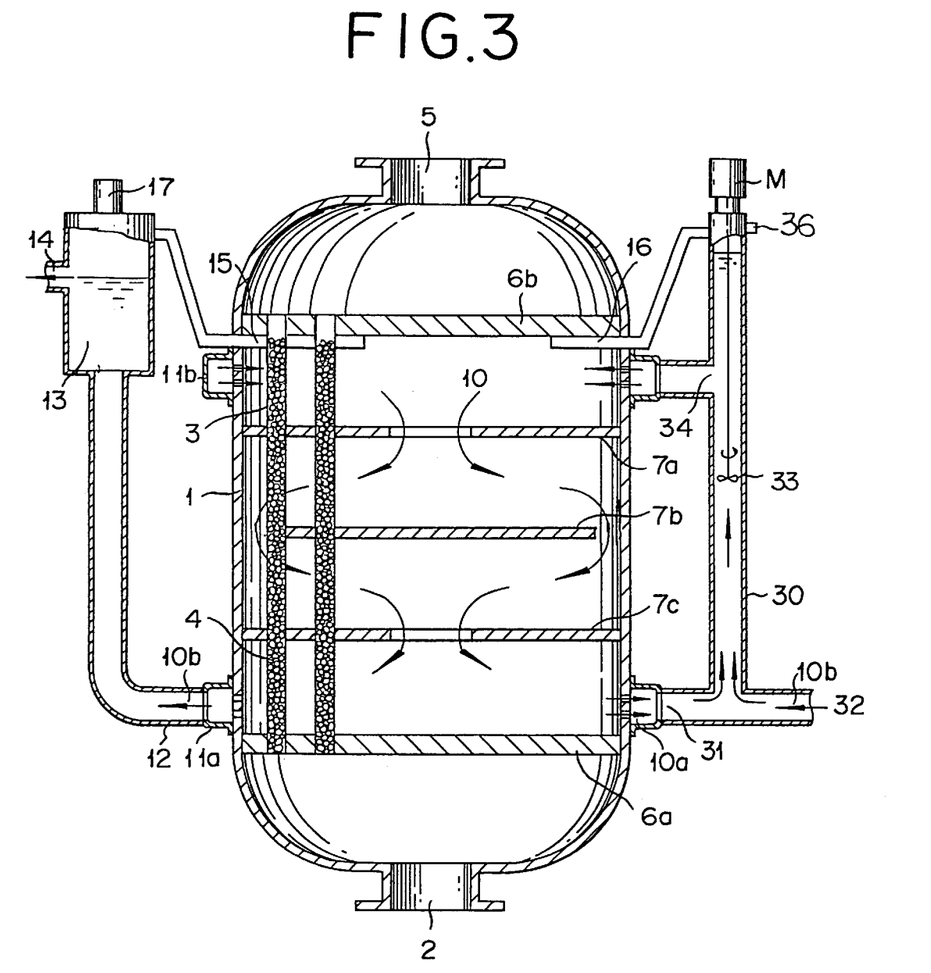
FIG. 3 is a cross section roughly illustrating a reactor of another embodiment to be used for the reaction of catalytic gas phase oxidation according to this invention.

Then, the case of implementing this invention by introducing the heating medium in the down-flow will be described below with reference to FIG. 3. Likewise in the configuration of FIG. 3, this invention causes the cooled heating medium 10b to be introduced into the circulation device 30 through the heating medium inlet 32 disposed in the proximity of heating medium circulating inlet 31. In this case, the heating medium which has been extracted through the heating medium outlet 12 disposed in the annular conduit 11a is pushed up to a heating medium discharge pot 13 disposed above an upper tube sheet 6b of the shell 1 of the reactor and then discharged out of the system via a nozzle 14. In this case, the cooled heating medium is supplied through the heating medium inlet 32 in the same amount as the heating medium 10b discharged out of the system by means of the heating medium discharge pot 13. Consequently, the shell 1 of the reactor is enabled to retain the state of being filled with the heating medium 10. Incidentally, the heating medium 10b mentioned above and the heating medium 10a which has been recovered through the heating medium circulating inlet 31 are mixed and drawn up by means of a pump 33 such as an axial pump or a volute pump and/or an agitator and are then supplied to the shell 1 of the reactor through the heating medium outlet 34. The amount of the heating medium to be supplied may be adjusted in the aforementioned range of the amount of the heating medium to be circulated.

The method of this invention, in any of the modes of embodiment, is preferable to implement the supply of the heating medium to the shell 1 side of the reactor and the extraction thereof from the shell 1 side respectively through the medium of a pair of the annular conduits 11a, 11b disposed in the upper and the lower peripheral part of the reactor. The circulation device, when necessary, may be provided with not less than two heating medium circulation inlets and heating medium discharge outlets. As a result, the heating medium may be circulated to the annular conduits through the plurality of portions of the annular device.

In implementing the method of this invention, the shell of the reactor is enabled to retain infallibly the state of being filled with the heating medium by disposing back pressure imparting means before and after the outlet of the heating medium 10b and exerting a fully satisfactory back pressure to the heating medium 10 flowing down the reaction tube. The method for extracting the heating medium 10b out of the shell 1 of the reactor is preferred to be capable of enabling the interior of the shell 1 of the reactor to retain the state of being filled with the heating medium 10. The provision of the back pressure imparting means ensures the retention of the state of being filled with the heating medium by exerting back pressure fully satisfactorily to the heating medium flowing down the reaction tube. As concrete examples of the back pressure imparting means, resistance orifice, valve, and heat exchanger may be cited.

Besides, when the gas introduced into the upper part of the reactor shell 1 as entrained by the heating medium during the supply of this heating medium collects in the shell side inner part of the reactor, it may be extracted through the upper part of the reactor shell 1 into the upper empty space part of a heating medium discharge pot 13 or the heating medium circulation device 30 via a pipe 15 laid on the outer periphery of the reactor or a pipe 16 inserted to the central part. By the conduit intended to extract the gas, the formation of the pool of gas in the reactor shell 1 which constitutes itself the cause for disrupting the uniform removal of the heat inside the reactor and inducing an abnormal reaction therein can be prevented. For example, the gas may be discharged through a gas discharge port 17 by causing the gas discharging conduit 15 disposed in the upper part of the shell of the reactor to communicate with the heating medium discharge pot 13 position in the upper level of the upper tube sheet of the reactor or the gas may be discharged through the gas discharge conduit 16 in the shell of the reactor into the upper empty space part of the circulation device 30 which is possessed of a gas discharge conduit 36 as illustrated in FIG. 3.

Figure 4:
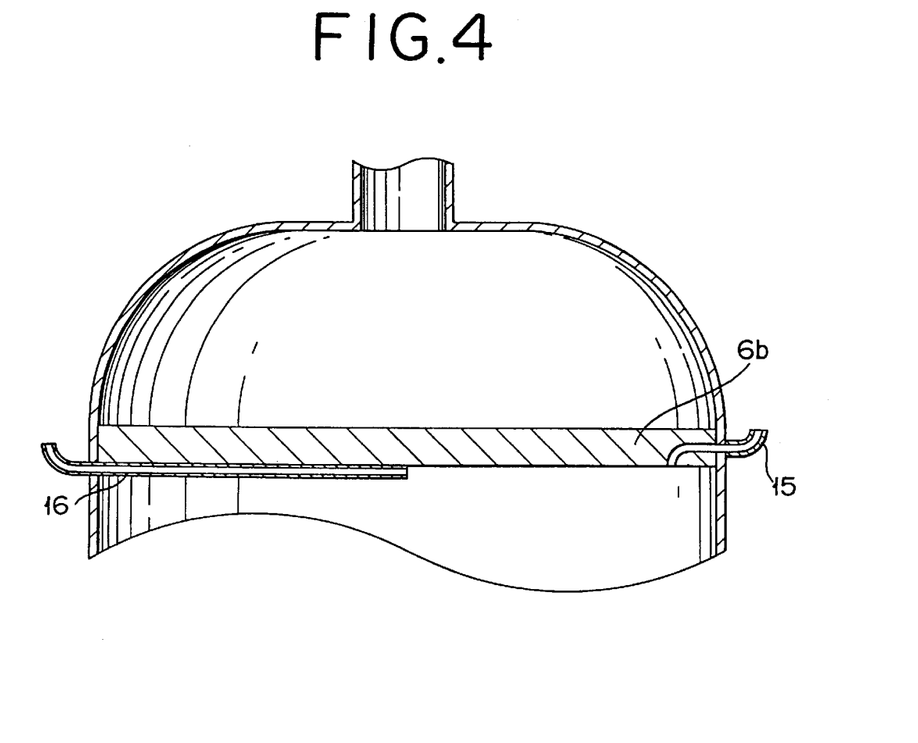
FIG. 4 is a partial cross section illustrating the layout of an upper tube sheet and a conduit for discharge of gas.

FIG. 4 illustrates an example of the disposition of a gas discharge conduit. As concerns the gas which collects upper part of the shell of the reactor, for example, the flow path 15 may be formed in an upper tube sheet 6b in the manner depicted in the diagram and allowed to continue into the exterior of the reactor. As concerns the gas which collects in the central part of the shell of the reactor, it suffices to dispose the gas discharge conduit 16 directly below the upper tube sheet 6b.

Now, the manner of extracting part of the heating medium which has circulated through the reactor shell 1 through the upper part of the circulation device 30 will be explained with reference to FIG. 5.

When the heating medium is circulated up-flow as illustrated in FIG. 5, for example, it may be extracted by the use of the pump 33 through the heating medium extraction port 12 formed in the upper part of the circulation device 30. It is commendable in this case to dispose a partition plate 37 capable of preventing the heating medium of interest from mingling with the heating medium 10b introduced through the heating medium introduction port 32 disposed in the lower part of the circulation device 30.

Now, the method for forming acrolein or methacrolein by the reaction of catalytic gas phase oxidation of propylene or isobutylene in accordance with the method of this invention will be described below with reference to FIG. 5.

The reaction of this invention for catalytic gas phase oxidation is effected by supplying the raw material gas to a catalyst 4 which fills reaction tubes 3. The raw material gas which results from mixing the raw materials for the reaction with air is supplied through a raw material gas supply port 2 into the reactor 1, allowed to flow down the interiors of the reaction tubes 3, oxidized in the reaction tubes and consequently converted into a reaction product, and discharged through a produced gas discharge port 5.

For the purpose of producing acrylic acid by subjecting a propylene-containing gas to the reaction of a two-step catalytic gas phase oxidation according to this invention, the oxidizing catalyst which is generally used for producing acrolein by subjecting a propylene-containing raw material gas to a reaction of gas phase oxidation can be used as the former-step catalyst, for example. As the latter-step catalyst which likewise is subjected to no particular restriction, the oxidizing catalyst which is generally used in producing acrylic acid by subjecting to gas phase oxidation a reaction gas containing mainly the acrolein obtained by the former step of the method for two-step catalytic gas phase oxidation can be used.

As concrete examples of the former-step catalyst, the catalysts represented by the general formula, $Mo_a$—$Bi_b$—$Fe_c$—$A_d$—$B_e$—$C_f$—$D_g$—$O_x$ (wherein Mo, Bi, and Fe respectively denote molybdenum, bismuth, and iron, A denotes at least one element selected from the group consisting of nickel and cobalt, B denotes at least one element selected from the group consisting of alkali metals and thallium, C denotes at least one element selected from the group consisting of phosphorus, niobium, manganese, cerium, tellurium, tungsten, antimony, and lead, D denotes at least one element selected from the group consisting of silicon, aluminum, zirconium, and titanium, and 0 denotes oxygen, a, b, c, d, e, f, g, and x respectively denotes the atomic ratios of Mo, Bi, Fe, A, B, C, D, and O, satisfying the respective ranges, b=0.1–10, c=0.1–10, d=2–20, e=0.001–5, f=$0_{14\ 5}$, and g=0–30 on the basis of a=12, and x denote the numerical value determined by the states of oxidation of the relevant elements), may be cited.

As concrete examples of the latter-step catalyst, the catalysts represented by the general formula, $Mo_a$—$V_b$—$W_c$—$Cu_d$—$A_e$—$B_f$—$C_g$—$O_x$ (wherein Mo denotes molybdenum, V denotes vanadium, W denotes tungsten, Cu denotes copper, A denotes at least one element selected from the group consisting of antimony, bismuth, tin, niobium, cobalt, iron, nickel, and chromium, B denotes at least one element selected from the group consisting of alkali metals, alkaline earth metals, and thallium, C denotes at least one element selected from the group consisting of silicon, aluminum, zirconium, and cerium, and O denotes oxygen, a, b, c, d, e, f, g, and x respectively denote the atomic ratios of Mo, V, W. Cu. A, B, C, and O, satisfying the ranges, b=2–14, c=0–12, d=0.1–5, e=0–5, f=0–5, and g=0–20 on the basis of a=12, and x denotes a numerical value determined by the states of oxidation of the relevant elements), may be cited.

As the catalyst to be used in obtaining methacrylic acid by subjecting isobutylene, t-butanol, or methyl-t-butyl ether according to this invention, the oxidizing catalyst which is generally used as the former-step catalyst, for example, in the production of methacrolein by the reaction of gas phase oxidation of a raw material gas containing isobutylene can be used. As the latter-step catalyst which likewise is subject to no particular restriction, the oxidizing catalyst which is generally used in the production of methacrylic acid by the gas phase oxidation of a reaction gas mainly containing the methacrolein obtained by the former step in the method for the two-step catalytic gas phase oxidation can be used.

Specifically, as concrete examples of the former-step catalyst preferably used herein, the catalysts represented by the general formula, $Mo_a$—$W_b$—$Bi_c$—$Fe_d$—$A_e$—$B_f$—$C_g$—$D_h$—$O_x$ (wherein Mo, W, and Bi respectively denote molybdenum, tungsten, and bismuth, Fe denotes iron, A denotes nickel and/or cobalt, B denotes at least one element selected from the group consisting of alkali metals, alkaline earth metals, and thallium, C denotes at least one element selected from the group consisting of phosphorus, tellurium, antimony, tin, cerium, lead, niobium, manganese, and zinc, niobium, manganese, D denotes at least one element selected from the group consisting of silicon, aluminum, titanium, and zirconium, and O denotes oxygen, a, b, c, d, e, f, g, h, and x respectively denote the atomic ratios of Mo, W. Bi, Fe, A, B, C, D, and O, satisfying the respective ranges, b=0–10, c=0.1–10, d=0.1–20, e=2–20, f=0.001–10, g=0–4, and h=0–30 on the basis of a=12, and x denote the numerical value determined by the states of oxidation of the relevant elements), may be cited.

The latter-step catalyst does not need to be particularly restricted but is only required to be formed of one or more oxide catalysts containing molybdenum and phosphorus as main components. A preferred example of the latter-step catalyst is phosphomolybdic acid type heteropoly acid or a metal salt, for example. As concrete examples of the latter-step catalyst, the catalysts represented by the general formula, $Mo_a$—$P_b$—$A_c$—$B_d$—$C_e$—$D_f$—$O_x$ (wherein Mo denotes molybdenum, P denotes phosphorus, A denotes at least one element selected from the group consisting of arsenic, antimony, germanium, bismuth, zirconium, and selenium, B denotes at least one element selected from the group consisting of copper, iron, chromium, nickel, manganese, cobalt, tin, silver, zinc, palladium, rhodium, and tellurium, C denotes at least one element selected from the group consisting of vanadium, tungsten, and niobium, D denotes at least one element selected from the group consisting of alkali metals, alkaline earth metals, and thallium, and O denotes oxygen, a, b c, d, e, f, and x respectively denote the atomic ratios of Mo, P, A, B, C, D, and O, satisfying the ranges, b=0.5—4, c=0—5, d=0—3, e=0—4, and f=0.01—4 on the basis of a=12, and x denotes a numerical value determined by the states of oxidation of the relevant elements), may be cited.

The catalyst does not need to be particularly discriminated on account of shape. It may assume any of such shapes as spheres, circular columns, and cylinders. This catalyst may be formed by such methods as carrying molding, extrusion molding, and tabletting molding. A catalyst produced in the form of depositing a catalytic substance on a refractory carrier is also useful.

The reaction of gas phase oxidation of propylene or isobutylene with molecular oxygen can be carried out under conditions which are adopted by methods heretofore known to the art. To take propylene, for example, the propylene concentration in the raw material gas is in the range of 3–15 vol. %, the ratio of molecular oxygen to propylene in the range of 1–3, and the remainder of the raw material gas comprises nitrogen, steam, carbon oxides, propane, etc.

Air is advantageously used as the source for the molecular oxygen. An oxygen-enriched air or pure oxygen may be used instead, when necessary. The supply of this molecular oxygen source is effected by the one-pass method or the recycling method. Preferably, the reaction temperature is in the range of 250–450° C., the reaction pressure in the range of from normal pressure to 5 atmospheres, and the space velocity in the range 500–3000 h−1 (STP).

In the case of the reaction of gas phase catalytic oxidation of isobutylene, the isobutylene concentration in the raw material gas is in the range of 1–10 vol. %, the concentration of molecular oxygen relative to isobutylene is in the range of 3–20 vol. %, the concentration of steam is in the range of 0–60 vol. %, and the remainder of the raw material gas comprises nitrogen, carbon oxides, etc. Air is advantageously used as the source for the molecular oxygen. An oxygen-enriched air or pure oxygen may be used instead, when necessary. Preferably, the reaction temperature is in the range of 250–450° C., the reaction pressure in the range of from normal pressure to 5 atmospheres, and the space velocity in the range 300–5000 h−1 (STP).

Under the conditions mentioned above, the raw material gas is introduced into the former-step catalyst layer and the produced gas containing (meth)acrolein mainly, either in its unmodified form or after addition thereto of air, steam, etc., is introduced into the latter-step catalyst layer to produce (meth)acrylic acid.

Specifically, for the purpose of forming acrylic acid, a mixed gas formed, when necessary, by adding air, oxygen, or steam to the acrolein-containing gas obtained by the former-step reaction mentioned above is supplied at a reaction temperature (catalyst temperature in the reactor) in the range of 100–380° C., preferably 150–350° C., at a space velocity in the range of 300–5,000 hr−1 (STP) into a second heat exchanger type shell-and-tube reactor having the bundled tubes in the shell thereof packed with the oxide catalyst mentioned above (latter-step catalyst) and subjecting the mixed gas to a latter-step reaction to afford acrylic acid.

Then, for the purpose of forming methacrylic acid, a mixed gas formed, when necessary, by adding air, oxygen, or steam to the methacrolein-containing gas obtained by the former-step reaction mentioned above is supplied at a reaction temperature (catalyst temperature in the reactor) in the range of 100–380° C., preferably 150–350° C., at a space velocity in the range of 300–5,000 hr−1 (STP) into a second heat exchanger type shell-and-tube reactor having the bundled tubes in the shell thereof packed with the oxide catalyst mentioned above (latter-step catalyst) containing molybdenum and phosphorus and subjecting the mixed gas to a latter-step reaction to afford methacrylic acid. By applying this method of the present invention to the conventional reactor which is provided with an intermediate tube sheet partitioning the interior thereof into an upper and a lower chamber, the production of (meth)acrylic acid may be attained.

The reaction tubes used herein in terms of material, size, number, and arrangement may be selected from among various kinds of reaction tubes known to the art.

As an additional factor, the reactor shell 1 is preferred to be provided therein with a plurality of baffle plates 7a, 7b, and 7c. The disposition of these baffle plates results in facilitating the exchange of heat between the reaction tubes 3 and the heating medium 10.

The heating medium to be circulated in the reactor shell 1 may be any of the known kinds of heating medium. Fused salt, niter, and phenyl ether type heating medium which is a Dowtherm type organic heating medium, for example, are useful.

According to this invention, maleic anhydride can be produced from the raw material gas of benzene or butane in the known reaction system using the known catalyst and phthalic anhydride can be produced from the raw material gas of xylene and/or naphthalene in the known reaction system using the known catalyst.

According to this invention, only by effecting the introduction of a heating medium into the reactor prior to use for circulation at a predetermined position in the circulation device, it is made possible to uniformize the temperature distribution of the heating medium very efficiently and enable the existing equipment to enjoy a prominent feature of being used effectively in its unmodified form. Consequently, it is made possible to reduce uniformly the hot spot temperatures of the reaction tubes, secure stable reaction, allow highly efficient prevention of the catalyst from deterioration, accomplish extension of the service life of the catalyst, and exalt the rate of selection of the product aimed at.

Now, this invention will be described more specifically below with reference to working examples.

EXAMPLE 1 OF PRODUCTION OF CATALYST

In 150 ml of purified water kept heated and stirred, 100 kg of ammonium molybdate, 6.3 kg of ammonium paratungstate, and 13.7 kg of nickel nitrate were dissolved. To the resultant solution, an aqueous nitrate solution prepared by mixing a solution of 68.7 kg of cobalt nitrate in 100 liters of purified water, a solution of 19 kg of ferric nitrate in 30 liters of purified water, and a solution of 27.5 kg of bismuth nitrate in 30 liters of purified water incorporating therein 6 liters concentrated nitric acid was added dropwise. Subsequently, a solution of 14.2 kg of an aqueous 20 mass. % silica gel solution and 0.29 kg of potassium nitrate in 15 liters of purified water was further added thereto. The suspension thus obtained was heated and stirred till vaporization to dryness and then dried and pulverized. The produced powder was molded into cylinders 5 mm in diameter and fired at 460° C. for six hours as swept with air to afford a catalyst. This catalyst was obtained in a prescribed amount by repeating this process. This catalyst was found to have this molar composition, Mo 12, Bi 1.2, Fe 1, Co 5, Ni 1, W 0.5, Si 1, K 0.06.

EXAMPLE 2 OF PRODUCTION OF CATALYST

In 50 liters of purified water kept heated and stirred, 100 kg of ammonium molybdate, 12.7 kg of ammonium paratungstate, and 27.6 kg of ammonium metavanadate were dissolved. To the resultant solution, a solution of 20.5 kg of copper nitrate and 1.4 kg of antimony trioxide in 50 liters of purified water was added. The mixed solution and 350 kg of a silica-alumina carrier 5 mm in average particle diameter added thereto were evaporated to dryness together to effect deposition of a catalyst component on the carrier. The deposited catalyst component was fired at 400° C. for six hours to form a catalyst. This catalyst in a prescribed amount was obtained by repeating this process. This catalyst was found to have this molar composition, Mo 12, V 5.0, W 1.0, Cu 1.8, Sb 0.2.

EXAMPLE 1

By the use of a shell-and-tube type reactor constructed as illustrated in FIG. 1, a reaction of catalytic gas phase oxidation was carried out under the following conditions.

A shell-and-tube type heat exchanger possessing 9000 reaction tubes of steel each measuring 3.5 m in length, 25.0 mm in inside diameter, and 29.0 mm in outside diameter was used. The reactor shell was a cylindrical container 4000 mm in inside diameter and the reaction tubes were uniformly disposed throughout the entire cross-sectional area of the container.

The reaction tubes 3 were each packed with 1520 ml of the reaction catalyst of Example 1 production of catalyst. A raw material gas composed of 7.0 vol. % of propylene, 12.6 vol. % of oxygen, 10.0 vol. % of steam, and 70.4 vol. % of an inert gas formed of nitrogen, etc. was fed through the raw material supply port 2. The contact time of the reaction gas was set at 3.0 seconds (reduced to STP) and a pump was used as the heating medium circulation device of the reactor. The heating medium used herein was composed of 50 mass. % of potassium nitrate and 50 mass. % of sodium nitrite. The heating medium was circulated through the medium of the annular conduit 11a which, for the purpose of enabling the heating medium to be uniformly introduced into the shell of the reactor from the entire circumference of the annular conduit, was provided with rows of openings having a center distance of 250 mm, each row consisting of 50 openings having a width of 20% of average center distance and a value of opening length/orientation width in the range of 5–8. The heating medium emanating from the annular conduit 11a meandered through the baffle plates 7a and 7b and reached the annular conduits 11b. It was taken out of the system via the heating medium discharge port 12 of the annular conduit 11b, cooled in the heat exchanger (not shown), and then circulated from the heating medium introduction port 32 into the circulation device 30.

Incidentally, temperature of heating medium inlet 32, and heating medium being introduced into the shell of the reactor (T2) at the heating medium outlet 34 of the circulation device 30.

Figure 6:
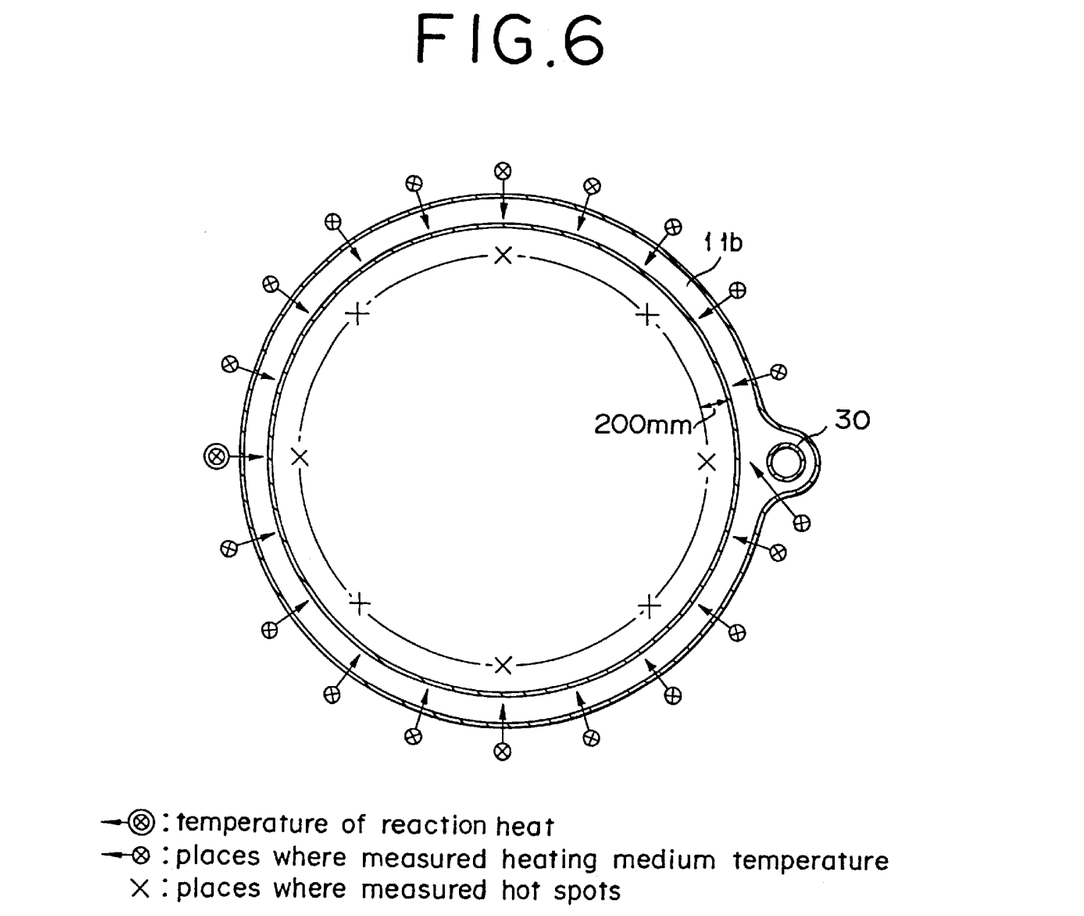
FIG. 6 is an explanatory diagram depicting one example of the measurement of temperature distribution in an inlet annular conduit of the reactor to be used in Example 6.

The reaction temperature (T3) measured with a thermometer installed at a position of 180° relative to the heating medium circulation device in the annular conduit 11a on the side of feeding the heating medium to the reactor was adjusted to 320° C. The temperature distribution in the inlet annular conduit of the reactor was measured at intervals of 18° (at a total of 20 points) as illustrated in FIG. 6. The temperature of cooling heating medium to be introduced into a circulation device was measured with a thermometer at the heating medium inlet 32. The results are shown in Table 1.

EXAMPLE 2

The same test items as used in Example 1 were determined by following the procedure of Example 1 while changing the difference between the temperature of cooling heating medium (T1) and the heating medium being introduced into the shell of the reactor (T2) to 100° C. and the ratio of flow rate of the cooling heating medium and the heating medium in the reactor to 1.5. The results are shown in Table 1.

EXAMPLE 3

A shell-and-tube type reactor possessed of 9000 reaction tubes of steel each measuring 6 m in length, 25.0 mm in inside diameter, and 29.0 mm in outside diameter and provided with an intermediate tube sheet into two chambers having a pair of annual conduits per each chamber was used. A reactor shell used herein was a cylindrical container 4000 mm inside diameter and had the reaction tubes uniformly disposed throughout the entire cross section thereof.

The reaction tubes were first packed with 1520 ml of the catalyst of Example 1 of production of catalyst as a former-step catalyst, packed thereon with 250 ml of spheres of alundum 5 mm in diameter intended for cooling the reaction gas, and further packed thereon with 1100 ml of the catalyst of Example 2 of production of catalyst as the latter-step catalyst. A raw material gas composed of 7.0 vol. % of propylene, 12.6 vol. % of oxygen, 10.0 vol. % of steam, and 70.4 vol. % of an inert gas formed of nitrogen, etc. was supplied to the former-step catalyst at such a flow rate as to give rise to a contact time of 3.0 seconds (reduced to STP) with the former-step catalyst. A pump was used as the heating medium circulation device for the reactor. The heating medium used herein was composed of 50 mass. % of potassium nitrate and 50 mass. % of sodium nitrite. The introduction and the discharge of the heating medium were carried out through the medium of annular conduits, which, for the purpose of enabling the heating medium to be uniformly introduced into the shell of the reactor from the entire circumference of the annular conduit, were provided above and below an intermediate tube sheet with rows of openings having a center distance of 250 mm, each row consisting of 50 openings having a width of 20% of average center distance and a value of opening length/orientation width in the range of 5–8. The heating medium emanated from the lower annular conduits above and below the intermediate tube sheet, meandered through the baffle plates, and then reached the upper annular conduits. The heating medium which had departed from the reactor was taken out of the system through the heating medium discharge port of the upper annular conduit, cooled in the heat exchanger, and then circulated to the circulation device through the heating medium introduction port.

Incidentally, temperature of heating medium inlet 32, and heating medium being introduced into the shell of the reactor (T2) at the heating medium outlet 34 of the circulation device 30.

The reaction temperature (T3) measured with a thermometer installed at a position of 180° relative to the heating medium circulation device in the annular conduit on the side for feeding the heating medium to the reactor, was adjusted to 320° C. for the former step and to 300° C. for the latter step. The temperature distribution in the inlet annular conduit of the reactor was measured at intervals of 18° (at a total of 20 points) as illustrated in FIG. 6. The temperature of cooling heating medium to be introduced into a circulation device was measured with a thermometer at the heating medium inlet of each chamber. The results are shown in Table 2.

EXAMPLE 4

The same test items as used in Example 3 were determined by following the procedure of Example 3 while changing the temperature difference between the cooling heating medium (T1) and the heating medium being introduced into the shell of the reactor (T2) to 100° C. and the ratio of flow rates of the cooling heating medium and the heating medium in the reactor to 1.5. The results are shown in Table 2.

COMPARATIVE EXAMPLE 1

The same test items as used in Example 1 were determined by following the procedure of Example 1 while changing the temperature difference between the cooling heating medium (T1) and the heating medium being introduced into the shell of the reactor (T2) to 13° C. and the ratio of flow rates of the cooling heating medium and the heating medium in the reactor to 11.5. The results are shown in Table 1.

COMPARATIVE EXAMPLE 2

The same test items as used in Example 1 were determined by following the procedure of Example 1 while changing the temperature difference between the cooling heating medium (T1) and the heating medium being introduced into the shell of the reactor (T2) to 160° C. and the ratio of flow rates of the cooling heating medium and the heating medium in the reactor to 0.9. The results are shown in Table 1.

COMPARATIVE EXAMPLE 3

The same test items as used in Example 1 were determined by following the procedure of Example 1 while substituting the outlet of the heating medium circulation device for the portion for introducing the cooling heating medium. The results are shown in Table 1.

COMPARATIVE EXAMPLE 4

The same test items as used in Example 3 were determined by following the procedure of Example 3 while changing the temperature difference between the cooling heating medium (T1) and heating medium absorbed the reaction heat in the reactor shell (T2) to 13° C. and the ratio of flow rates of the cooling heating medium and the heating medium in the reactor to 11.5. The results are shown in Table 2.

COMPARATIVE EXAMPLE 5

The same test items as used in Example 3 were determined by following the procedure of Example 3 while changing the temperature difference between the cooling heating medium (T1) and the heating medium being introduced into the shell of the reactor (T2) to 160° C. and the ratio of flow rates of the cooling heating medium and the heating medium in the reactor to 0.9. The results are shown in Table 2. In Table 2, the mark "-" denotes omission of determination.

COMPARATIVE EXAMPLE 6

The same test items as used in Example 3 were determined by following the procedure of Example 3 while substituting the outlet of the heating medium circulation device for the portion for introducing the cooling heating medium. The results are shown in Table 2.

TABLE 1

| Conditions | Example 1 | Example 2 | Comparative Example 1 | Comparative Example 2 | Comparative Example 3 |
|---|---|---|---|---|---|
| Place for addition of cooling heating medium (relative to heating medium circulation device) | Inlet | Inlet | Inlet | Inlet | Outlet |
| Temp. of heating medium after cooling at heating medium inlet 32 [° C.]: T1 | 300.0 | 220.0 | 307.0 | 160.0 | 300.0 |
| Temp. of the heating medium being introduced into the shell at the heating medium outlet 34 [° C.]: T2 | 320.0 | 320.0 | 319.2 | 320.9 | 315.4 |
| Reaction temperature [° C.]: T3 | 320.0 | 320.0 | 320.0 | 320.0 | 320.0 |
| Difference between T1 and T2 [° C.] | 20.0 | 100.0 | 12.2 | 160.9 | 15.4 |
| Amount of heating medium circulated in reactor [m$^3$/h] | 3300 | 3300 | 3300 | 3300 | 3300 |
| Ratio of volumes of cooling heating medium and heating medium in reactor [%] | 7.5 | 1.5 | 11.5 | 0.9 | 7.5 |
| Difference of temperature (+ side) from reaction temperature [° C.]* | +0.1 | +0.1 | +1.8 | +1.1 | +1.3 |
| Difference of temperature (− side) from reaction temperature [° C.]* | 0 | 0 | −0.8 | −2.8 | −5.2 |
| Hot spot temperature (maximum) [° C.]** | 380.0 | 380.2 | 383.4 | 382.3 | 382.8 |
| Hot spot temperature (minimum) [° C.]** | 379.8 | 379.9 | 378.2 | 374.5 | 369.7 |

*Difference of temperature between reaction temperature and maximum or minimum temperature in the distribution of FIG. 6.
**Maximum or minimum at eight sites of determination

TABLE 2

| Conditions | Example 3 | Example 4 | Comparative Example 4 | Comparative Example 5 | Comparative Example 6 |
|---|---|---|---|---|---|
| Place for addition of cooling heating medium (relative to heating medium circulation device) | Inlet | Inlet | Inlet | Inlet | Outlet |
| Former-step catalyst | | | | | |
| Temp. of heating medium after cooling at heating medium outlet 34 [° C.]: T1 | 300.0 | 220.0 | 307.0 | 160.0 | 300.0 |
| Temp. of the heating medium being introduced into the shell at the heating medium outlet 34 [° C.]: T2 | 320.0 | 320.0 | 319.4 | 321.1 | 315.8 |
| Reaction temperature [° C.]: T3 | 320.0 | 320.0 | 320.0 | 320.0 | 320.0 |
| Difference between T1 and T2 [° C.] | 20.0 | 100.0 | 12.4 | 161.1 | 15.8 |
| Amount of heating medium circulated in reactor [m³/h] | 3300 | 3300 | 3300 | 3300 | 3300 |
| Ratio of volumes of cooling heating medium and heating medium in reactor [%] | 7.5 | 1.5 | 11.5 | 0.9 | 7.5 |
| Difference of temperature (+ side) from reaction temperature [° C.]* | +0.1 | +0.1 | +1.9 | +1.2 | +1.2 |
| Difference of temperature (− side) from reaction temperature [° C.]* | 0 | 0 | −0.9 | −2.7 | 5.1 |
| Hot spot temperature (maximum) [° C.]** | 380.2 | 380.1 | 383.5 | 382.5 | 382.6 |
| Hot spot temperature (minimum) [° C.]** | 379.9 | 379.8 | 378.0 | 374.4 | 369.8 |
| Latter-step catalyst | | | | | |
| Temp. of heating medium after cooling at heating medium outlet 34 [° C.]: T1 | 285.0 | 200.0 | 287.0 | — | 285.0 |
| Temp. of the heating medium being introduced into the shell at the heating medium outlet 34 [° C.]: T2 | 300.1 | 300.1 | 299.5 | — | 294.8 |
| Reaction temperature [° C.]: T3 | 300.0 | 300.0 | 300.0 | — | 300.0 |
| Difference between T1 and T2 [° C.] | 15.1 | 100.1 | 12.5 | — | 9.8 |
| Amount of heating medium circulated in reactor [m³/h] | 1000 | 1000 | 3300 | — | 1000 |
| Ratio of volumes of cooling heating medium and heating medium in reactor [%] | 30.0 | 4.5 | 11.5 | — | 30.0 |
| Difference of temperature (+ side) from reaction temperature [° C.]* | +0.2 | +0.1 | +1.7 | — | +1.5 |
| Difference of temperature (− side) from reaction temperature [° C.]* | 0 | 0 | −0.9 | — | −5.6 |
| Hot spot temperature (maximum) [° C.]** | 325.2 | 325.1 | 328.7 | — | 382.8 |
| Hot spot temperature (minimum) [° C.]** | 325.0 | 324.8 | 323.0 | — | 313.9 |

*Difference of temperature between reaction temperature and maximum or minimum temperature in the distribution of FIG. 6.
**Maximum or minimum at eight sites of determination

RESULTS (1) In Example 1, by resulting in adjustment the temperature of heating medium after cooling and introducing into the reactor and the temperature thereof as shown FIG. 1, the difference between the reaction temperature and the temperature in a varying determination had an upper limit of 0.1° C. and a lower limit of 0° C., whereas the upper limit temperature was 1.3° C. and the lower limit temperature was −5.2° C. when the cooled heating medium was circulated to the heating medium outlet of the heating medium circulation medium. This fact indicates that the heating medium was circulated with a temperature width of 6.5° C. in the shell of the reactor.

Owing to this thermal unevenness, the highest value of hot spot was 382.8° C. and the lowest value thereof was 369.7° C., the difference reaching 13.1° C. In contrast, the temperature variation of the hot spots in Example 1 was only 0.2° C.

(2) By resulting in adjustment the temperature of heating medium after cooling and introducing into the reactor and the temperature thereof as shown FIG. 1, when the difference between the temperature of the cooling heating medium and the reaction temperature was less than 15° C., it was not possible to obtain a heating medium having uniform heat distribution even when the ratio of flow rates of the cooling heating medium and the heating medium in the reactor was set at 11.5%. As a result, the difference between the reaction temperature and the temperature in a varying determination had an upper limit of 1.8° C. and a lower limit of 0.8° C. Owing to this thermal unevenness, the highest value of hot spot was 383.4° C. and the lowest value thereof was 378.2° C., the difference reaching 5.2° C.

(3) By resulting in adjustment the temperature of heating medium after cooling and introducing into the reactor and the temperature thereof as shown FIG. 1, when the difference between the temperature of the cooling heating medium and the reaction temperature exceeded 150° C., the difference between the reaction temperature and the temperature in a varying determination was wider than in Comparative Example 1, i.e. the upper limit was 1.1° C. and the lower limit was −2.8° C. and the width of variation was 3.9° C. Owing to this thermal unevenness, the highest value of hot spot was 382.3° C. and the lowest value thereof was 374.5° C. and the different there between was 7.8° C.

(4) The same trend as observed in (1)–(3) mentioned above was observed also in the single reactors of Example 3 and Example 4.

What is claimed is:

1. In the reaction of catalytic gas phase oxidation by means of a shell-and-tube reactor adapted to circulate a heating medium to the shell of said reactor through the medium of a circulation device connecting an annular conduit connected thereto, a method for, the catalytic gas phase oxidation characterized by, wherein subjecting a part of said heating medium extracted from said shell of the reactor to heat exchange, introducing said heating medium resulting from the heat exchange into the proximity of a heating medium circulation inlet on the inlet side of said circulation device or the annular conduit on the outlet side of said reactor, setting the flow rate of said heating medium after said heat exchange in the range of 2–40 vol. % based on the flow rate of said heating medium within the shell of said reactor, and setting the temperature difference between said heating medium after the heat exchange and said heating medium being introduced into the shell of the reactor in the range of 15–150° C.

2. A method according to claim 1, wherein the heating medium after said heat exchange has resulted from gas-liquid separation.

3. A method according to claim 1, wherein the introduction or discharge of said heating medium into or out of the shell of said reactor is carried out through the medium of a conduit disposed annularly outside said reactor and said conduit is possessed of a plurality of rows of openings capable of passing said heating medium and the width of said openings is in the range of 5–50% of the center distance and the numerical value of opening length/opening width is in the range of 0.2–20.

4. A method according to claim 3, wherein at least one of said plurality of rows of openings is possessed of not less than two openings.

5. A method according to claim 1, wherein said circulation device is possessed of not less than two heating medium circulation inlets and/or heating medium discharge outlets.

6. A method according to claim 1, wherein said heating medium is given a back pressure or the gas collecting in the upper part of the shell of said reactor is discharged from within said shell.

7. A method according to claim 1, wherein said reaction of catalytic gas phase oxidation produces (meth)acrylic acid and/or (meth)acrolein.

8. A method according to claim 1, wherein said reaction of catalytic gas phase oxidation is carried out in a reactor partitioned with an intermediate tube sheet.

* * * * *